US011214629B2

(12) United States Patent
Li et al.

(10) Patent No.: US 11,214,629 B2
(45) Date of Patent: Jan. 4, 2022

(54) METHOD FOR PREPARING SHORT-CLUSTERED DEXTRIN

(71) Applicant: Jiangnan University, Wuxi (CN)

(72) Inventors: Zhaofeng Li, Nuxi (CN); Zhengbiao Gu, Nuxi (CN); Yang Li, Nuxi (CN); Caiming Li, Nuxi (CN); Li Cheng, Nuxi (CN); Yan Hong, Nuxi (CN)

(73) Assignee: Jiangnan University, Wuxi (CN)

( * ) Notice: Subject to any disclaimer, the term of this patent is extended or adjusted under 35 U.S.C. 154(b) by 10 days.

(21) Appl. No.: 16/884,340

(22) Filed: May 27, 2020

(65) Prior Publication Data

US 2020/0283546 A1  Sep. 10, 2020

Related U.S. Application Data

(63) Continuation of application No. PCT/CN2019/089311, filed on May 30, 2019.

(30) Foreign Application Priority Data

Aug. 13, 2018 (CN) .......................... 201810915843.2

(51) Int. Cl.
*C08B 30/18* (2006.01)
*C12P 19/18* (2006.01)
*C08B 30/20* (2006.01)

(52) U.S. Cl.
CPC .............. *C08B 30/18* (2013.01); *C08B 30/20* (2013.01); *C12P 19/18* (2013.01)

(58) Field of Classification Search
None
See application file for complete search history.

(56) References Cited

U.S. PATENT DOCUMENTS

2010/0099864 A1* 4/2010 van der Maarel ...... A23L 33/10
536/102

FOREIGN PATENT DOCUMENTS

| CN | 1233286 A   | 10/1999 |
|----|-------------|---------|
| CN | 101631474 A | 1/2010  |
| CN | 104293865 A | 1/2015  |
| CN | 107119026 A | 9/2017  |
| CN | 108047340 A | 5/2018  |
| CN | 108949861 A | 12/2018 |

OTHER PUBLICATIONS

Yu et al., "Two 1,4-α-glucan branching enzymes successively rearrange glycosidic bonds: A novel synergistic approach for reducing starch digestibility" Carbohydrate Polymers vol. 262 p. 117968 https://doi.org/10.1016/j.carbpol.2021.117968 (Year: 2021).*
PCT/CN2019/089311 ISR ISA210 dated Sep. 17, 2019.
Fan,Qin et al. Overexpression of Starch Branching Enzyme from Thermomonospora curvata and Its Catalytic Mechanism Research,Modern Food Science and Technology, 2016, vol. 32, No. 6.

* cited by examiner

*Primary Examiner* — Eric Olson
(74) *Attorney, Agent, or Firm* — Ipro, PLLC; Na Xu

(57) ABSTRACT

The present disclosure discloses a method for preparing short-clustered dextrin, and belongs to the field of biomodified starch. The method includes: collaboratively modifying to-be-modified starch by adopting Ro-GBE and Gt-GBE. The present disclosure utilizes two starch branching enzymes from different microorganism sources to collaboratively modify corn starch. The Ro-GBE is firstly added for pretreatment, then the Gt-GBE is added. The Ro-GBE catalyzes the to-be-modified starch to form a chain segment structure which is more conducive to further utilization for the Gt-GBE, thin and long starch molecule is transformed into short-clustered structure under the catalysis of Gt-GBE, and thus the slow digestibility of modified products is more obvious. Further, by changing the addition amount of Ro-GBE, modification time and the state of to-be-modified starch, the synergistic effect between the two branching enzyme is promoted, and the branching degree is improved, thus the SDS content and the RS content are further improved.

7 Claims, No Drawings

Specification includes a Sequence Listing.

SEQUENCE LISTING

<160> NUMBER OF SEQ ID NOS: 2

<210> SEQ ID NO 1
<211> LENGTH: 1860
<212> TYPE: DNA
<213> ORGANISM: Rhodothermus obamensi

<400> SEQUENCE: 1

```
agctggctca cggaagaaga catccggcgc tgggaaagcg gtacgttcta cgacagttac      60
cgaaagctgg gcgcccatcc cgacgacgaa ggcacctggt tctgcgtctg ggcgccgcat     120
gccgatggcg tctcggtgct cggagcgttc aacgactgga atccggaggc caacccgctg     180
gagcgctacg gcggcggcct gtgggccggt tacgtaccgg gagcgcgccc gggccacacc     240
tacaagtatc gcatccggca cggcttctat caggccgaca agacggatcc ctacgccttc     300
gccatggagc cgcctaccgg cagtcccatc gaagggctgg cctccatcat cacgcggctc     360
gactacacct ggcacgacga cgaatggatg cggcgccgga agggtccggc cagccttttac     420 gagccggttt ccatctacga ggtacatctg ggctcctggc gtcacaaacg gcccggcgag     480
tccttctctt accgggagat tgccgagccg ctggccgact acgtgcagga gatgggcttc     540
acgcacgtgg agctgctgcc cgtcatggaa catccctact acggctcctg gggctatcag     600
gtggtgggct actacgcccc aacgtttcgc tacggatcac cccaggacct gatgtacctg     660
atcgactacc tgcaccagcg cggcatcggc gtcatcctcg actgggtccc gagccacttt     720
gcggccgatc cccagggact ggttttcttc gacgggacca cactcttcga atacgacgat     780
cccaagatgc gctatcaccc tgactggggt acgtatgtgt tcgattacaa caagccgggc     840
gtacgcaact ttctgatttc caacgcactt ttctggctcg aaaagtacca cgtcgacggg     900
ctgcgcgtcg atgcggtggc ttctatgctc taccgggact actcacgcaa ggagtggaca     960
cccaacatct tcggcggccg tgaaaacctg gaggccattg atttcatcaa gaaattcaac    1020
gaaacggtct acctgcactt ccccgaggcc atgacgatcg ccgaggagtc gacggcctgg    1080
cccggcgtgt cggccccccac ctacaacaac ggtctgggct tcctctacaa gtggaacatg    1140
ggctggatgc acgacacgct ggactacatc agcgcgatcc catctaccg caagtatcac    1200 cacgacgagc tgaccttctc gctctggtac gccttttcgg agcactacgt cctgccgctc    1260
tcgcacgacg aggtggtgca cggcaagggc tcgctctggg gtaaaatgcc cggcgacgac    1320
tggcagaagg cagccaactt gcgcctgctc tttggccaca tgtggggcca tccgggcaaa    1380
aaactgctct tcatgggcgg cgagttcggc cagcaccacg agtggaacca cgacacgcag    1440
ctcgaatggc acctgctgga ccagccctac catcgaggta ttcagctgtg ggtgtgcgat    1500
ctgaaccacc tctaccgtac gaatccggcc ctctggcacg acggaccgga agggttcgag    1560
tggatcgact tcagcgaccg cgaccagagc gtgatctgtt acctgcgcaa gaatgccggc    1620
cgcatgctgc tgttcgtgct gaactttacg cccgtgccac gcgagcacta ccgcgtgggc    1680
gtgccgatcg gtggcccctg gcacgaggtg ctcaacagcg acgcggtggc ctacggcggg    1740
agcgggatgg gcaacttcgg ccgcgtcgag gcggtgcccg agtcctggca cggccgcccc    1800
ttccacttag agctgacgct tccccccgctg gccgccctca tcctggagcc ggagcacggg    1860
```

<210> SEQ ID NO 2
<211> LENGTH: 1926
<212> TYPE: DNA
<213> ORGANISM: Geobacillus thermoglucosidans

<400> SEQUENCE: 2

-continued

```
agcgttgtcc ctccgaccga tctggaaatt tatttatttc acgaaggcag cttatataaa    60
agttatgaat tgtttggcgc gcatgtgata aaacaaaacg acgttgtcgg aacccggttt   120
tgcgtatggg ctccgcatgc gcggcaagtg cggttagtcg gcagttttaa tgactggaac   180
ggaactaatt ttaatcttgt aaaagtaagt aatcaaggtg tatggacgat ttttattccg   240
gaaaacttgg aagggcattt atataaatac gaaattacca ctagcgatgg aaatgtcgtg   300
ttaaaagcag atccatacgc gtttcactcc gaattgcgcc cccgtactgc ctccatcgtc   360
tacgacataa aaggttatca atggaatgac caaacatggc gacggaagaa acagcgaaag   420
cgaatatatg accagccttt gttcatttat gagcttcact tcggttcgtg gaaaaagaaa   480
gaaaacggca attttatac atatcgggag atggcagatg agttacttcc atacgtgatg   540
gaacatggtt ttacccacat tgaattgctt ccgctcgttg aacatccgct tgaccgctcc   600
tggggatatc aaggaacagg ttattattca gcaacaagcc gctacgggac gccgcatgat   660
ttgatgcatt ttattgatcg cttccatcaa gcgggcattg gcgtcatttt cgattgggtt   720
cccggccact tttgcaaaga tgaacatgga ttatacatgt ttgatggagc accgacatac   780
gaatatgaca acatacaaga tcgggaaaat ggcgaatggg gcacggcgaa ttttgatctt   840
ggcaagccgg aagtccgcag ctttttgatt tccaatgcgt tgttttggat ggaatatttc   900
cacgtcgacg gatttcgggt ggatgcggtg gccaatatgc tgtattggcc aaatagagag   960
gcagcacagc aaaacccgca tgctgttcag tttttgcaaa aattaaatga gaccgtattt  1020
gcgcatgacc cgggcatatt gatgattgcc gaagattcga cggaatggcc gctcgtcact  1080
gctccaacgt atgccggagg gctggggttt aactataaat ggaacatggg gtggatgaac  1140
gatatttaa catatatgga aacggcgccg gagaagcgaa aacatgtgca caataaagta  1200
acctttccc ttttgtacgc gtattcggaa aattttattt tacctttttc ccacgatgag  1260
gtcgtgcatg gaaaaaaatc gctgctaaat aaaatgccgg ggacgtatga ggaaaagttt  1320
gcacaattaa ggctgctgta tgggtatttg ctaacacatc ccggcaagaa actattgttt  1380
atgggcggcg aatttgccca gtttgatgag tggaaggatg cagagcagct ggattggatg  1440
cttttgatt tcgagatgca ccagaaaatg aatatgtacg tgaaagcatt attgaaatgt  1500
tataagcgct gcaaatcttt gtatgagcta gaccattctc cagacgggtt tgagtggatt  1560
gatgttcata acgctgaaca aagtattttc tcatttgtcc gcagaggaaa aaagaaaac  1620
gatttgcttg ttgtcgtgtg caattttacc agtaaagtgt atcacgatta taaagttggc  1680
gttccgctat ttgccaaata ccgggaaatc atcagcagcg atgcggccaa attcgggggg  1740
tggggcaatg tcaatgcaaa gccggttgcg gcgagcaaag aaccgtttca tggaaagccg  1800
tatcatattc gcatgacggt tccgccgttt ggcatttcca tttaagacc agtgaaaaaa  1860
cggggggaga gaagcgttga tggcaaagaa aaagtgcatc gccatgttat tggcgggagg  1920
gcaagg                                                             1926
```

METHOD FOR PREPARING SHORT-CLUSTERED DEXTRIN

TECHNICAL FIELD

The present disclosure relates to a method for preparing short-clustered dextrin, and belongs to the field of bio-modified starch.

BACKGROUND

Starch is a main component of fruits, seeds, tubers and tuberous roots of green plants, and is the most abundant storage polysaccharide on the earth. As the main energy source for humans and most animals, starch is widely used in food, medicine, chemistry and other industry fields. According to the time of releasing glucose during the starch digestion in human intestine, the starch is divided into rapidly digestible starch (RDS), slowly digestible starch (SDS) and resistant starch (RS). The RDS is the starch rapidly digested and absorbed in small intestines within the digestion time of 20 min. The SDS is the starch digested and absorbed completely but slowly in the small intestines, within the digestion time of 20 to 120 min. The RS is the starch that still cannot be digested and absorbed in the small intestine within 120 min, which is similar to dietary fiber that can only be fermented and utilized by microorganisms in large intestine.

In the resident diet, the "quality" and "quantity" of the starch directly influence the regulation of blood glucose. With the improvement of people's living standard, the incidence of chronic diseases such as diabetes increases gradually in recent years, so that it is imperative to study and prepare slowly digestible or resistant starch products which can maintain satiety, continuously supply energy, avoid severe fluctuation of the blood glucose, and meanwhile have an adjuvant therapy efficacy on non-insulin-dependent diabetes and cardiovascular diseases.

The molecular structure of starch can be changed by utilizing physical, chemical or biological methods currently, and the part of RDS can be transformed into the SDS so as to meet the need of healthy diet. The biological enzyme method achieves the purpose of improving the starch digestibility mainly by changing the starch structure itself. Previous studies mostly utilize a single enzyme to modify starch, but the SDS content in modified starch is relatively low. Several double-enzyme treatment methods reported in current literatures mainly include: transglucosylase and β-amylase collaborative modification, maltose α-amylase and transglucosylase collaborative modification, starch branching enzyme and amylosucrase collaborative modification, etc., but the product yield thereof is relatively low. In order to improve the product yield as far as possible, a step of washing with ethanol is usually adopted in preparation technology, which causes a larger loss of modified product, relatively longer modification time and other problems.

SUMMARY

In order to solve the current problems of low product yield of short-clustered dextrin and long modification time, the present disclosure provides a method for preparing short-clustered dextrin.

Ro-GBE from *Rhodothermus obamensi* belongs to a glycoside hydrolase family 57, Gt-GBE from *Geobacillus thermoglucosidans* belongs to a glycoside hydrolase family 13, and both can catalyze three transglycosylation reactions (inter-chain transfer, intra-chain transfer and cyclization reactions), and are the key enzymes for synthesizing glycogens and amylopectin. They can firstly cut off the α-1,4 glycosidic linkage of the starch chain, and then transfer the cut-off chain segment to a receptor chain with an α-1,6 glycosidic linkage to form a new branch, so that the branching degree increases, and the digestion rate of modified starch lowers. Catalytic mechanisms of the two enzymes are both conductive to generation of the short-clustered dextrin.

The first objective of the present disclosure is to provide a method for preparing short-clustered dextrin. The method includes: collaborative modification on starch by adopting the starch branching enzyme Ro-GBE from *Rhodothermus obamensi* and the starch branching enzyme Gt-GBE from *Geobacillus thermoglucosidans*.

Optionally, the method for preparing the short-clustered dextrin includes: Firstly adding the Ro-GBE to pretreat the to-be-modified starch, and then adding the Gt-GBE to continuously modify the pretreated starch.

Optionally, in the step of firstly adding the Ro-GBE to pretreat the to-be-modified starch, the addition amount of the Ro-GBE is 25 to 40 U/g dry-basis starch.

Optionally, in the step of then adding the Gt-GBE to continuously modify the pretreated starch, the addition amount of the Gt-GBE is 20 to 30 U/g dry-basis starch.

Optionally, the to-be-modified starch is in a gelatinized state. In the gelatinized state, the condition for modifying the starch by the Ro-GBE is a constant-temperature reaction for 10 to 120 min at 60 to 65° C. After Ro-GBE deactivation, the reaction is continued for 8 to 12 h at 50° C. after the Gt-GBE is added.

Optionally, in the gelatinized state, a condition for modifying gelatinized corn starch by the Ro-GBE is a constant-temperature reaction for 10 min at 60 to 65° C. After enzyme deactivation, the reaction is continued for 8 to 12 h at 50° C. after the Gt-GBE is added.

Optionally, the to-be-modified starch is in a granular state. In the granular state, a condition for modifying the to-be-modified starch by the Ro-GBE is a constant-temperature reaction for 2 to 12 h at 60 to 65° C. After enzyme deactivation, the reaction is continued for 8 to 12 h at 50° C. after the Gt-GBE is added.

Optionally, in the granular state, a condition for modifying granular corn starch by the Ro-GBE is a constant-temperature reaction for 12 h at 60 to 65° C. After enzyme deactivation, the reaction is continued for 12 h at 50° C. after the Gt-GBE is added.

Optionally, a concentration of to-be-modified starch slurry is 10% to 25%.

Optionally, a pH of the to-be-modified starch slurry is 6.5 to 7.5.

The second objective of the present disclosure is to provide short-clustered dextrin prepared by utilizing any of the above methods.

The third objective of the present disclosure is to provide applications of the above short-clustered dextrin to prepare food and medicines for preventing and delaying the general population of non-insulin-dependent diabetes mellitus.

The present disclosure has the following beneficial effects.

Two starch branching enzymes from different sources are utilized to collaboratively treat on corn starch, the Ro-GBE is firstly added for pretreatment, then the Gt-GBE is added, the Ro-GBE catalyzes the to-be-modified starch to form a chain segment structure that is more conducive to further utilization by the Gt-GBE, thin and long starch molecules are transformed into short-clustered branch structures under the treatment of the Gt-GBE, and thus the slow digestibility of modified products is more obvious. Further, by changing the addition amount of the Ro-GBE, modification time and the state of the to-be-modified starch, collaborative action between the two enzyme is promoted, the branching degree of modified starch is improved, and the SDS content and the RS content are further improved, so that the digestion rate lowers, and a new idea is provided for preparation of the short-clustered dextrin through biological modification.

DETAILED DESCRIPTION

In order to make the objectives, technical solutions and advantages of the present disclosure is clearer, embodiments of the present disclosure will be further described in detail below with reference to figures.

The following examples are illustrated with an example of to-be-modified corn starch, and the modification process thereof is free of a step of washing with ethanol.

First, the Englyst in-vitro simulated digestion method adopted in the following Examples and Comparative Examples is introduced as follows.

A starch digestion rate is determined with reference to the Englyst in-vitro simulated digestion method.

Porcine pancreatic amylase (3 g, activity 8×USP; and product number P7545, Sigma) and 20 mL deionized water are fully mixed evenly and centrifuged for 10 min at 3500×g. 15 mL supernatant is taken to be fully mixed with 1.1 mL diastatic enzyme (product number A-7095, Sigma) to prepare a mixed enzyme, which is freshly prepared just before use. Starch (0.6 g) is taken and gelatinized in a boiling water bath with 5 mL sodium acetate buffer solution (0.25 M, pH 5.2), and then preheated for 10 min in a water bath shaker (37° C., 160 r/min). Guar gum (50 mg) and pepsin (10 mL, 50 mg/10 mL HCl) are added to react for 30 min. Glass beads and sodium acetate buffer solution (5 mL) are added in sequence to continue to react for 30 min. The mixed enzyme (5 mL) is added. The sample (0.125 mL) is taken into 5 mL of 66% ethanol for enzyme deactivation after accurately timing for 20 min and 120 min, respectively. Centrifugation is conducted for 5 min at 3500 r/min. The supernatant (0.05 mL) is taken to determine the content of glucose with a glucokinase method.

Specific formulas are as follows.

RDS (%)=($G20-G0$)×0.9×100

SDS (%)=($G120-G20$)×0.9×100

RS (%)=100−RDS (%)−SDS (%)

where G0 denotes the content of free glucose in starch; G20 denotes the content of glucose generated after hydrolysis for 20 min; and G120 denotes the content of glucose generated after hydrolysis for 120 min.

Second, two starch branching enzymes Gt-GBE and Ro-GBE from different sources adopted by the present application are introduced as follows.

A gene sequence of the starch branching enzyme Ro-GBE from *Rhodothermus obamensi* is shown as SEQ ID NO.1; and A gene sequence of the starch branching enzyme Gt-GBE from *Geobacillus thermoglucosidans* is shown as SEQ ID NO.2.

The situations of separate modification by double enzymes in a double-enzyme collaborative modification method adopted by the present application are firstly introduced below.

Example 1

Effects of Separate Modification by Gt-GBE on the Content of Rapidly Digestible Starch in Modified Product Corn starch is dissolved in water to obtain 10% starch slurry. After gelatinization with boiling water, the Gt-GBE (25 U/g dry-basis starch) is added to treat for 2, 4, 6, 8 and 10 h at a constant temperature of 50° C. A boiling water bath is conducted to terminate the reaction. Freeze drying is conducted to obtain modified samples. The digestibility of modified starch measured with reference to the Englyst in-vitro simulated digestion method is as shown in Table 1. A control group represents the digestibility of gelatinized corn starch before modification treatment.

Results show that under action of the separate Gt-GBE, compared with the control group, when modification treatment is conducted for 10 h, the RDS content reduces by $$20.8\% \left(\frac{77.9 - 61.7}{77.9} \times 100\%\right),$$

the SDS content increases by $$134\% \left(\frac{21.6 - 9.2}{9.2} \times 100\%\right),$$

and the RS content increases by $$28.5\% \left(\frac{16.7 - 13.0}{13.0} \times 100\%\right).$$

It can be known that during the separate modification by the Gt-GBE, the SDS proportion increases significantly. The reason may be that the slow digestibility of the product is improved significantly by a highly-branched structure generated under action of the Gt-GBE.

TABLE 1

Effects of modification time of Gt-GBE on the digestibility of modified product

| Test projects | Modification time (h) | RDS content (%) | SDS content (%) | RS content (%) |
|---|---|---|---|---|
| Control group | 0 | 77.9 ± 0.8 | 9.2 ± 0.7 | 13.0 ± 0.5 |
| Solution 1 | 2 | 71.5 ± 1.1 | 15.9 ± 0.9 | 12.6 ± 1.2 |
| Solution 2 | 4 | 69.2 ± 0.7 | 19.0 ± 0.8 | 11.8 ± 1.2 |
| Solution 3 | 6 | 67.5 ± 1.1 | 18.9 ± 0.9 | 13.6 ± 0.9 |
| Solution 4 | 8 | 64.5 ± 0.9 | 18.6 ± 0.5 | 16.9 ± 0.9 |
| Solution 5 | 10 | 61.7 ± 0.9 | 21.6 ± 0.5 | 16.7 ± 0.9 |

Example 2

Effects of Separate Modification by Ro-GBE on the Content of Rapidly Digestible Starch in Modified Product Corn starch is dissolved in water to obtain 25% starch slurry. After gelatinization with boiling water, Ro-GBE (30 U/g dry-basis starch) is added to treat for 2, 4, 6, 8 and 10 h at a constant temperature of 65° C. A boiling water bath is conducted to terminate a reaction. Freeze drying is conducted to obtain modified samples. The digestibility of modified starch measured with reference to the Englyst in-vitro simulated digestion method is as shown in Table 2. A control group represents the digestibility of gelatinized corn starch before modification treatment.

Results show that under action of the separate Ro-GBE, compared with the control group, when the treatment is conducted for 2 h, the RDS content reduces by $$12.5\% \left( \frac{77.9 - 68.2}{77.9} \times 100\% \right),$$

but subsequently as the treatment time increases, the RDS content increases. And when treatment is conducted for 10 h, the RDS content even exceeds the control group where the Ro-GBE is not added for modification. The SDS content increases by $$9.78\% \left( \frac{10.1 - 9.2}{9.2} \times 100\% \right),$$

subsequently as the treatment time increases, the SDS content increases by $$42.4\% \left( \frac{13.1 - 9.2}{9.2} \times 100\% \right)$$

when the treatment is conducted for 4 h, but when continuing to prolong the treatment time to 10 h, the SDS content decreases, and even lower than the control group where the Ro-GBE is not added for modification. And the RS content increases by $$66.9\% \left( \frac{21.7 - 13.0}{13.0} \times 100\% \right),$$

and subsequently as the treatment time increases, the RS content slightly fluctuates.

Compared with Example 1, the modification effect within relatively short Ro-GBE treatment time is better. And the RDS content increases again with the prolonging of treatment time. The reason may be that the hydrolysis of the Ro-GBE is relatively high, so that more free short chains and small-molecule saccharides are generated when the treatment time is relatively longer, which are not conductive to the slow digestibility of the product.

TABLE 2

Effects of modification time of Ro-GBE on the digestibility of modified product

| Test projects | Modification time (h) | RDS content (%) | SDS content (%) | RS content (%) |
| --- | --- | --- | --- | --- |
| Control group | 0 | 77.9 ± 0.8 | 9.2 ± 0.7 | 13.0 ± 0.5 |
| Solution 1 | 2 | 68.2 ± 0.3 | 10.1 ± 0.8 | 21.7 ± 0.9 |
| Solution 2 | 4 | 69.4 ± 0.9 | 13.1 ± 1.1 | 17.5 ± 0.9 |
| Solution 3 | 6 | 74.4 ± 0.6 | 6.3 ± 0.8 | 19.3 ± 1.1 |
| Solution 4 | 8 | 77.4 ± 0.6 | 5.4 ± 0.9 | 17.2 ± 0.8 |
| Solution 5 | 10 | 78.5 ± 0.4 | 6.9 ± 0.7 | 14.6 ± 1.2 |

A double-enzyme collaborative modification method adopted by the present application is introduced below to respectively analyze the effects of the addition amount of the Ro-GBE, the modification time of the Ro-GBE. And treating on granular starch with the Ro-GBE in a double-enzyme collaborative modification method is introduced in detail.

Control groups in all Examples and Comparative Examples of the present disclosure represent the digestibility of gelatinized corn starch before modification treatment. But the RDS content, the SDS content and the RS content therein are slightly different, within an allowable error range.

Example 3

Effects of the Addition Amount of Ro-GBE on the Content of Rapidly Digestible Starch in Double-Enzyme Collaboratively-Modified Product Corn starch is dissolved in water to obtain 25% starch slurry. After gelatinization with boiling water, the Ro-GBE is added to treat for 2 h at a constant temperature of 65° C. A boiling water bath is conducted to terminate the reaction. Gt-GBE (25 U/g dry-basis starch) is added to modify for 10 h at a constant temperature of 50° C. Then the reaction is terminated. Freeze drying is conducted to obtain modified samples. The digestibility of modified starch measured with reference to the Englyst in-vitro simulated digestion method is shown in Table 3. The control group represents the digestibility of gelatinized corn starch before modification treatment.

Results show that compared with Example 1, in the present example, the RDS content reduces by $$31.6\% \left( \frac{61.7 - 42.2}{61.7} \times 100\% \right)$$

at most, the SDS content increases by $$52.8\% \left( \frac{33.0 - 21.6}{21.6} \times 100\% \right)$$

at most, and the RS content increases by $$55.6\% \left( \frac{26.3 - 16.9}{16.9} \times 100\% \right)$$

at most; and compared with Example 2, the RDS content reduces by $$38.1\% \left( \frac{68.2 - 42.2}{68.2} \times 100\% \right)$$

at most, the SDS content increases by $$152\% \left( \frac{33.0 - 13.1}{13.1} \times 100\% \right)$$

at most, and the RS content increases by $$21.2\% \left( \frac{26.3 - 21.7}{21.7} \times 100\% \right)$$

at most.

Compared with single-enzyme single-stage modification, the effect of double-enzyme two-stage modification is more significant. The RDS content reduces significantly, and the SDS content and the RS content increases to different degrees. It is speculated that the intermediate product formed with the Ro-GBE (30 U/g dry-basis starch) is more conductive to continuous treatment of the Gt-GBE so as to form highly-branched shortly-clustered dextrin. Table 3 Effects of addition amount of Ro-GBE on the digestibility of double-enzyme modified

TABLE 3

Effects of addition amount of Ro-GBE on the digestibility of double-enzyme modified product

| Test projects | Enzyme addition amount (U/g dry-basis starch) | RDS content (%) | SDS content (%) | RS content (%) |
|---|---|---|---|---|
| Control group | 0 | 77.9 ± 0.8 | 9.2 ± 0.7 | 13.0 ± 0.5 |
| Solution 1 | 25 | 61.7 ± 0.9 | 17.7 ± 0.5 | 20.6 ± 0.9 |
| Solution 2 | 30 | 42.2 ± 0.7 | 33.0 ± 0.8 | 24.8 ± 1.2 |
| Solution 3 | 35 | 45.9 ± 1.1 | 27.8 ± 0.9 | 26.3 ± 0.9 |
| Solution 4 | 40 | 50.5 ± 1.0 | 23.2 ± 0.7 | 26.3 ± 0.6 |

Example 4

Effects of the Modification Time of Ro-GBE on the Content of Rapidly Digestible Starch in Double-Enzyme Collaboratively-Modified Product Corn starch is dissolved in water to obtain 25% starch slurry. After gelatinization with boiling water, Ro-GBE (30 U/g dry-basis starch) is added to modify at a constant temperature of 65° C. A boiling water bath is conducted to terminate the reaction. Gt-GBE (25 U/g dry-basis starch) is added to modify for 10 h at a constant temperature of 50° C. Then the reaction is terminated. Freeze drying is conducted to obtain modified samples. The digestibility of modified starch measured with reference to the Englyst in-vitro simulated digestion method is shown in Table 4. The control group represents the digestibility of gelatinized corn starch before modification treatment.

Results show that compared with the control group, in a double-enzyme collaboratively-modified product with Ro-GBE treatment time of 2 h, the RDS content reduces by $$46.9\% \left( \frac{77.9 - 39.8}{77.9} \times 100\% \right),$$

the SDS content increases by $$226\% \left( \frac{30.0 - 9.2}{9.2} \times 100\% \right),$$

and the RS content increases by $$89.9\% \left( \frac{30.2 - 13.0}{13.0} \times 100\% \right).$$

Compared with the optimal modified products in Example 1 and Example 2, the RDS content reduces by $$35.5\% \left( \frac{61.7 - 39.8}{61.7} \times 100\% \right) \text{ and}$$

$$41.6\% \left( \frac{68.2 - 39.8}{68.2} \times 100\% \right)$$

respectively. It is shown that under collaborative modification of two branching enzymes from different sources, the changes in the fine structure of starch is more conductive to the improvement of slow digestibility thereof. The RDS content reduces significantly, and the proportions of SDS and RS both increases significantly.

TABLE 4

Effects of modification time of Ro-GBE on the digestibility of double-enzyme modified product

| Test projects | Modification time (h) | RDS content (%) | SDS content (%) | RS content (%) |
|---|---|---|---|---|
| Control group | 0 | 77.9 ± 0.8 | 9.2 ± 0.7 | 13.0 ± 0.5 |
| Solution 1 | 2 | 39.8 ± 0.3 | 30.0 ± 0.8 | 30.2 ± 0.9 |
| Solution 2 | 4 | 47.4 ± 0.8 | 20.1 ± 0.9 | 32.5 ± 0.4 |
| Solution 3 | 6 | 49.6 ± 0.7 | 23.3 ± 0.9 | 27.1 ± 1.0 |
| Solution 4 | 8 | 57.9 ± 0.6 | 28.4 ± 0.6 | 13.7 ± 1.0 |
| Solution 5 | 10 | 60.6 ± 0.6 | 26.9 ± 0.8 | 12.5 ± 1.0 |

Example 5

Effects of Further Shortening of Ro-GBE Modification Time on the Content of Rapidly Digestible Starch in Double-Enzyme Collaboratively-Modified Product Corn starch is dissolved in water to obtain 25% starch slurry. After gelatinization with boiling water, Ro-GBE (30 U/g dry-basis starch) is added to modify at a constant temperature of 65° C. A boiling water bath is conducted to terminate the reaction. Gt-GBE (25 U/g dry-basis starch) is added to modify for 10 h at a constant temperature of 50° C. Then the reaction is terminated. Freeze drying is conducted to obtain modified samples. The digestibility of modified starch measured with reference to the Englyst in-vitro simulated digestion method is shown in Table 5. The control group represents the digestibility of gelatinized corn starch before modification treatment.

Results show that although the treatment time of Ro-GBE is shortened to 10 min, the RDS content in a double-enzyme collaboratively-modified product may still be kept at the level of about 40%. It is shown that the modification efficiency of Ro-GBE is relatively high, and the significant effect may be haven within the relatively short time. Moreover, to sum up, the treatment of Ro-GBE within relatively short time is not only conductive to further action of Gt-GBE, but also has an advantage in saving energy.

TABLE 5

Effects of further shortening of modification time of Ro-GBE on the digestibility of double-enzyme modified product

| Test projects | Modification time (min) | RDS content (%) | SDS content (%) | RS content (%) |
|---|---|---|---|---|
| Control group | 0 | 77.9 ± 0.8 | 9.2 ± 0.7 | 13.0 ± 0.5 |
| Solution 1 | 10 | 39.9 ± 0.6 | 29.0 ± 0.8 | 31.1 ± 0.9 |
| Solution 2 | 20 | 40.5 ± 0.8 | 20.1 ± 1.1 | 39.4 ± 0.7 |
| Solution 3 | 30 | 39.4 ± 0.7 | 26.6 ± 1.9 | 34.0 ± 1.0 |
| Solution 4 | 60 | 40.8 ± 0.6 | 25.4 ± 0.6 | 33.8 ± 1.2 |
| Solution 5 | 120 | 43.8 ± 0.3 | 28.0 ± 0.5 | 28.2 ± 1.1 |

Example 6

Effects of Treating Granular Starch with Ro-GBE on the Content of Rapidly Digestible Starch in Double-Enzyme Collaboratively-Modified Product Corn starch is dissolved in water to obtain 25% starch slurry. After preheating, Ro-GBE is added to modify at a constant temperature of 65° C. A boiling water bath is conducted to terminate the reaction. Gt-GBE (25 U/g dry-basis starch) is added to modify for 10 h at a constant temperature of 50° C. Then the reaction is terminated. Freeze drying is conducted to obtain modified samples. The digestibility of modified starch measured with reference to the Englyst in-vitro simulated digestion method is shown in Table 6.

According to Table 6-1 to Table 6-4, results show that when granular starch is treated with the Ro-GBE for 10 h, and with the increasing of the addition amount from 25 U/g to 30 U/g (referring to 6-1 and 6-2), the RDS content reduces by 10.7%. When the enzyme-added amount continues increasing to 35 U/g and 40 U/g, the RDS contents have no significant change.

According to Table 6-2, when the addition amount of Ro-GBE is 30 U/g, with the prolonging of the modification time to 10 h, the RDS content reduces to a minimum value of 41.9%, and the SDS content and the RS content increase to 26.8% and 31.3%, respectively.

Compared with Example 3 and Example 4, in a double-enzyme two-stage modification process, the change trends with the addition amount of Ro-GBE increasing are the same. Thus it can be seen that 30 U/g dry-basis starch is the optimal addition amount. But for the treatment of gelatinized starch, appropriate time is less than 2 h (it may be 10 to 60 min), and too long time will enhance hydrolysis, resulting in the increase in the RDS content. For the granular starch, the appropriate time is about 10 h. Since the protection of the crystal structure of granular starch, amylose and amylopectin are attacked more slowly by enzyme, and thus the better modification effect can be realized with relatively longer modification time.

TABLE 6-1

Effects of modification time on the digestibility of double-enzyme modified product

| Test projects | Enzyme addition amount (U/g dry-basis starch) | Modification time (h) | RDS content (%) | SDS content (%) | RS content (%) |
|---|---|---|---|---|---|
| Control group | 0 | 0 | 74.9 ± 0.8 | 9.2 ± 0.7 | 15.9 ± 0.5 |
| Solution 1 | 25 | 0 | 65.5 ± 0.9 | 19.7 ± 0.8 | 14.81 ± 0.4 |
| Solution 2 | 25 | 4 | 60.2 ± 0.4 | 21.8 ± 0.4 | 18.03 ± 0.4 |
| Solution 3 | 25 | 8 | 52.1 ± 0.8 | 22.8 ± 0.7 | 25.12 ± 0.4 |
| Solution 4 | 25 | 10 | 46.9 ± 0.9 | 26.8 ± 0.8 | 26.29 ± 0.5 |
| Solution 5 | 25 | 12 | 47.5 ± 0.7 | 26.2 ± 0.4 | 25.34 ± 0.4 |

TABLE 6-2

Effects of modification time on the digestibility of double-enzyme modified product

| Test projects | Enzyme addition amount (U/g dry-basis starch) | Modification time (h) | RDS content (%) | SDS content (%) | RS content (%) |
|---|---|---|---|---|---|
| Control group | 0 | 0 | 74.9 ± 0.8 | 9.2 ± 0.7 | 15.9 ± 0.5 |
| Solution 1 | 30 | 0 | 62.2 ± 0.3 | 21.7 ± 0.8 | 16.1 ± 0.9 |
| Solution 2 | 30 | 4 | 50.4 ± 0.8 | 19.8 ± 0.9 | 29.8 ± 0.4 |
| Solution 3 | 30 | 8 | 47.6 ± 0.7 | 22.2 ± 0.9 | 30.2 ± 1.0 |
| Solution 4 | 30 | 10 | 41.9 ± 0.6 | 26.8 ± 0.6 | 31.3 ± 1.0 |
| Solution 5 | 30 | 12 | 45.5 ± 0.6 | 24.2 ± 0.8 | 30.3 ± 1.1 |

TABLE 6-3

Effects of modification time on the digestibility of double-enzyme modified product

| Test projects | Enzyme addition amount (U/g dry-basis starch) | Modification time (h) | RDS content (%) | SDS content (%) | RS content (%) |
|---|---|---|---|---|---|
| Control group | 0 | 0 | 74.9 ± 0.8 | 9.2 ± 0.7 | 15.9 ± 0.5 |
| Solution 1 | 35 | 0 | 61.5 ± 0.6 | 21.1 ± 0.3 | 17.44 ± 0.2 |
| Solution 2 | 35 | 4 | 52.2 ± 0.7 | 23.4 ± 0.6 | 24.36 ± 1.0 |
| Solution 3 | 35 | 8 | 49.2 ± 0.5 | 22.4 ± 0.8 | 25.17 ± 0.8 |
| Solution 4 | 35 | 10 | 43.9 ± 1.1 | 28.0 ± 0.6 | 28.07 ± 0.8 |
| Solution 5 | 35 | 12 | 46.2 ± 1.1 | 27.20 ± 1.1 | 26.59 ± 0.4 |

TABLE 6-4

Effects of modification time on the digestibility of double-enzyme modified product

| Test projects | Enzyme addition amount (U/g dry-basis starch) | Modification time (h) | RDS content (%) | SDS content (%) | RS content (%) |
|---|---|---|---|---|---|
| Control group | 0 | 0 | 74.9 ± 0.8 | 9.2 ± 0.7 | 15.9 ± 0.5 |
| Solution 1 | 40 | 0 | 60.7 ± 0.9 | 18.7 ± 0.5 | 20.6 ± 0.9 |
| Solution 2 | 40 | 4 | 52.2 ± 0.7 | 23.0 ± 0.8 | 24.9 ± 1.2 |
| Solution 3 | 40 | 8 | 45.9 ± 1.1 | 25.8 ± 0.9 | 28.4 ± 0.9 |
| Solution 4 | 40 | 10 | 44.2 ± 1.1 | 26.9 ± 0.6 | 28.9 ± 1.4 |
| Solution 5 | 40 | 12 | 50.5 ± 1.0 | 23.2 ± 0.7 | 26.3 ± 0.6 |

In order to further prove the advantages of high product yield and short modification time of the short-clustered dextrin, the present application that adopts the two starch branching enzymes (Ro-GBE and Gt-GBE) is compared with the application that adopts the cyclodextrin glycosyltransferase (CGT) collaborative with Gt-GBE.

Comparative Example 1

Advantages of Modification with Ro-GBE Collaborative with Gt-GBE Over Modification with CGT Collaborative with Gt-GBE Corn starch is dissolved in water to obtain the 25% starch slurry. After gelatinization with boiling water, the CGT (3 U/g dry-basis starch) is added and the mixture reacts at a constant temperature of 45° C. for different time. A boiling water bath is conducted to terminate the reaction. Then the Gt-GBE (25 U/g dry-basis starch) is added. The reaction is continued at a constant temperature of 50° C. for 10 h. Then the reaction is terminated. Freeze drying is conducted to obtain modified samples. The determined in-vitro digestibility is shown in Table 7-1.

TABLE 7-1

Effects of reaction time on the digestibility of samples

| Test projects | Reaction time of CGT (h) | RDS content (%) | SDS content (%) | RS content (%) |
|---|---|---|---|---|
| Control group | 0 | 74.3 ± 0.6 | 9.8 ± 0.9 | 15.9 ± 0.5 |
| Solution 1 | 2 | 55.7 ± 0.8 | 17.1 ± 0.6 | 27.2 ± 0.5 |
| Solution 2 | 4 | 50.7 ± 0.6 | 16.3 ± 0.5 | 33.0 ± 0.9 |
| Solution 3 | 6 | 48.6 ± 0.9 | 15.2 ± 1.2 | 36.2 ± 1.1 |
| Solution 4 | 8 | 50.1 ± 0.8 | 12.9 ± 0.6 | 37.0 ± 0.6 |

According to Table 7-1, it can be known that with the CGT treatment for 6 h and continuous Gt-GBE treatment for 10 h, the RDS content in a product may reduce to 48.6%, the RS content may be improved to 36.2%, and in this case, the SDS content is 15.2%. Results show that when the reaction time of Gt-GBE is fixed, as the CGT-treatment time prolongs, the RS content increases, the RDS content reduces, but the SDS content shows a slightly reducing trend.

Compared with the modified starch obtained through the treatment of Ro-GBE collaborative with Gt-GBE, the present comparative example with the lowest RDS content is shown in Table 3, the lowest RDS content is higher by about $$15\% \left( \frac{48.6 - 42.2}{42.2} \times 100\% \right).$$

And the SDS content significantly reduces, the RS content significantly increases. The reason may be that under the treatment of CGT, the cyclization reaction plays a primary role, so that the content of formed cyclodextrin increases; and the cyclodextrin and highly-branched starch chains may form a V-shaped crystalline structure, but through re-gelatinization with a boiling water bath, the V-shaped crystalline structure will disappear, the SDS content is lowered, and only a better ability to resist digestion is shown.

It needs to be illustrated that since the CGT and the Ro-GBE are different enzymes, the present application compares their respective products under the optimal reaction conditions. The Ro-GBE is added to modify at a constant temperature of 65° C. in Example 3 and Example 4, and the CGT is added to modify at a constant temperature of 45° C. in the present example. Moreover, the addition amounts of CGT and Ro-GBE are also different. In order to further illustrate that the modification adopting the Ro-GBE collaborative with the Gt-GBE is superior to the modification adopting the CGT collaborative with the Gt-GBE. The Comparative Example 2 is provided below, and the addition amounts of CGT and Ro-GBE are set to be the same to conduct comparison.

Comparative Example 2

Corn starch is dissolved in water to obtain the 25% starch slurry. After gelatinization, the CGT (30 U/g dry-basis starch) is added and the mixture reacts at a constant temperature of 45° C. for different time. A boiling water bath is conducted to terminate the reaction. The Gt-GBE (25 U/g dry-basis starch) is added. The reaction is continued at a constant temperature of 50° C. for 10 h. Then the reaction is terminated. Freeze drying is conducted to obtain modified samples. As shown in Table 7-2, the determined in-vitro digestibility is provided.

TABLE 7-2

Effects of improving addition amount of CGT on the digestibility of samples

| Test projects | Reaction time of CGT (h) | RDS content (%) | SDS content (%) | RS content (%) |
|---|---|---|---|---|
| Control group | 0 | 74.3 ± 0.6 | 9.8 ± 0.9 | 15.9 ± 0.4 |
| Solution 1 | 2 | 57.1 ± 1.1 | 12.1 ± 0.4 | 30.8 ± 0.5 |
| Solution 2 | 4 | 52.3 ± 0.9 | 14.3 ± 0.5 | 33.4 ± 0.6 |
| Solution 3 | 6 | 51.4 ± 0.9 | 13.2 ± 1.1 | 35.4 ± 0.9 |
| Solution 4 | 8 | 49.5 ± 0.6 | 11.9 ± 0.7 | 38.6 ± 0.5 |

According to Table 7-2, it can be known that with the CGT treatment for 6 h and continuous Gt-GBE treatment for 8 h, the RDS content in modified sample may reduce to 49.5%, and the RS content may increase to 38.6%. In this case, the SDS content is 11.9%. Results show that when the reaction time of Gt-GBE is fixed, as the CGT-treatment time prolongs, the RS content increases, the RDS content reduces, but the SDS content shows a slightly reducing trend. This modification result is similar to that obtained through the CGT (3 U/g dry-basis starch) treatment, as shown in Table 7-1. Therefore, the excessive addition of CGT does not further have a better improving effect on digestibility.

Based on the data of above Comparative Example 1 and Comparative Example 2, compared with above Example 4, it can be known that the present application adopts the two starch branching enzymes (Ro-GBE and Gt-GBE) to conduct collaborative modification, which makes the modification time shorter and the product yield higher. when the treatment time is less than or equal to 2 h, the RDS content reduces to about 39.8%, the SDS content increases to about 30.0%, and the RS content increases to about 30.2%. While the existing modification adopting CGT collaborative with Gt-GBE needs the 6 h treatment so that the RDS content reduces to about 48.6%. But this data is still larger than the value of about 39.8%.

Although the SDS content has increased to a relatively high value of about 17.1% after 2 h treatment, which adopts the CGT collaborative with Gt-GBE, the SDS content shows a reducing trend as the treatment time continuously increases.

Thus, the present application adopts the two starch branching enzymes to conduct the modification, the modification time is shorter, and the product yield is relatively higher.

From the perspective of product structure, the modified starch obtained through the treatment of the two starch branching enzymes has the higher stability and slower digestion rate, and the more significant effect on maintaining glucose homeostasis.

What is claimed is:

1. A method for preparing short-clustered dextrin, comprising:
collaboratively treating to-be-modified starch by adding a starch branching enzyme Ro-GBE from *Rhodothermus obamensi* to pretreat the to-be-modified starch to obtain a pretreated starch, and then adding a starch branching enzyme Gt-GBE from *Geobacillus thermoglucosidans* to continuously modify the pretreated starch.

2. The method according to claim 1, wherein an addition amount of Ro-GBE is 25 to 40 U/g of dry-basis starch.

3. The method according to claim 1, wherein an addition amount of Gt-GBE is 20 to 30 U/g of dry-basis starch.

4. The method according to claim 1, wherein the to-be-modified starch is in a gelatinized state; and in the gelatinized state, a condition for modifying the to-be-modified starch with the Ro-GBE is the constant temperature of 60 to 65° C. for 10 to 120 min, and after enzyme deactivation, the Gt-GBE is added to continue to react for 8 to 12 h at 50° C.

5. The method according to claim 1, wherein the to-be-modified starch is in a granular state; and in the granular state, a condition for modifying the to-be-modified starch with the Ro-GBE is a constant-temperature reaction for 2 to 12 h at 60 to 65° C., and after enzyme deactivation, the Gt-GBE is added to continue to react for 8 to 12 h at 50° C.

6. The method according to claim 1, wherein a concentration of starch slurry of the to-be-modified starch is 10% to 25%.

7. The method according to claim 1, wherein a pH value of starch slurry of the to-be-modified starch is 6.5 to 7.5.

* * * * *